(12) United States Patent
Vale

(10) Patent No.: US 7,967,837 B2
(45) Date of Patent: *Jun. 28, 2011

(54) CATHETER

(75) Inventor: David Vale, Clontarf (IE)

(73) Assignee: Salviac Limited, Dublin (IE)

( * ) Notice: Subject to any disclaimer, the term of this patent is extended or adjusted under 35 U.S.C. 154(b) by 927 days.

This patent is subject to a terminal disclaimer.

(21) Appl. No.: 10/180,972

(22) Filed: Jun. 27, 2002

(65) Prior Publication Data

US 2003/0093110 A1 May 15, 2003

Related U.S. Application Data

(60) Provisional application No. 60/301,820, filed on Jul. 2, 2001.

(30) Foreign Application Priority Data

Jun. 27, 2001 (IE) .................................... 2001/0591

(51) Int. Cl.
*A61M 29/00* (2006.01)

(52) U.S. Cl. ...................................... 606/200

(58) Field of Classification Search .............. 606/200, 606/108, 110, 127, 159, 194–198; 604/103.04, 604/104–107; 623/1.11, 1.12

See application file for complete search history.

(56) References Cited

U.S. PATENT DOCUMENTS

| | | | |
|---|---|---|---|
| 4,494,531 A | | 1/1985 | Gianturco |
| 4,727,873 A | * | 3/1988 | Mobin-Uddin ............... 606/200 |
| 5,040,548 A | | 8/1991 | Yock |
| 5,147,379 A | * | 9/1992 | Sabbaghian et al. .......... 606/206 |
| 5,201,757 A | | 4/1993 | Heyn et al. |
| 5,224,953 A | | 7/1993 | Morgentaler |
| 5,350,395 A | | 9/1994 | Yock |
| 5,360,401 A | | 11/1994 | Turnland |
| 5,445,646 A | | 8/1995 | Euteneuer et al. |
| 5,451,233 A | | 9/1995 | Yock |
| 5,534,007 A | | 7/1996 | St. Germain et al. |
| 5,571,135 A | | 11/1996 | Fraser et al. |
| 5,593,418 A | | 1/1997 | Mollenauer |
| 5,649,953 A | | 7/1997 | Lefebvre |
| 5,662,703 A | | 9/1997 | Yurek et al. |
| 5,681,347 A | | 10/1997 | Cathcart et al. |

(Continued)

FOREIGN PATENT DOCUMENTS

EP 819411 A2 1/1998

(Continued)

OTHER PUBLICATIONS

Search Report dated Jun. 23, 2006.

*Primary Examiner* — Elizabeth Houston

(74) *Attorney, Agent, or Firm* — Sughrue Mion, PLLC; Jonathan Feuchtwang

(57) ABSTRACT

A delivery catheter 1 has a distal pod 2 for reception of an embolic protection filter 3. The filter 2 is moved from a retracted delivery configuration to an extended deployed configuration by a push wire 6 which has an engagement hoop 7 at the distal end. Retraction of a handle 9 has the effect of retracting the pod 3 relative to the push wire 6 and the engagement hoop 7 and the filter 2 is effectively deployed by pushing it out of the pod 3.

32 Claims, 9 Drawing Sheets

U.S. PATENT DOCUMENTS

| | | | |
|---|---|---|---|
| 5,690,644 A | 11/1997 | Yurek et al. | |
| 5,738,667 A | 4/1998 | Solar | |
| 5,776,171 A | 7/1998 | Klein et al. | |
| 5,817,101 A | 10/1998 | Fiedler | |
| 5,968,052 A | 10/1999 | Sullivan, III et al. | |
| 5,993,460 A | 11/1999 | Beitelia et al. | |
| 6,042,588 A | 3/2000 | Munsinger et al. | |
| 6,066,158 A * | 5/2000 | Engelson et al. | 606/200 |
| 6,113,608 A | 9/2000 | Monroe et al. | |
| 6,117,140 A | 9/2000 | Munsinger | |
| 6,120,522 A | 9/2000 | Vrba et al. | |
| 6,142,987 A | 11/2000 | Tsugita | |
| 6,146,389 A | 11/2000 | Geitz | |
| 6,146,415 A | 11/2000 | Fitz | |
| 6,165,167 A | 12/2000 | Delaloye | |
| 6,165,197 A | 12/2000 | Yock | |
| 6,171,327 B1 | 1/2001 | Daniel et al. | |
| 6,174,327 B1 | 1/2001 | Mertens et al. | |
| 6,179,859 B1 * | 1/2001 | Bates et al. | 606/200 |
| 6,228,110 B1 | 5/2001 | Munsinger | |
| 6,238,410 B1 | 5/2001 | Vrba et al. | |
| 6,245,012 B1 * | 6/2001 | Kleshinski | 623/1.11 |
| 6,254,628 B1 | 7/2001 | Wallace et al. | |
| 6,290,710 B1 | 9/2001 | Cryer et al. | |
| 6,346,116 B1 | 2/2002 | Brooks et al. | |
| 6,371,971 B1 * | 4/2002 | Tsugita et al. | 606/200 |
| 6,380,457 B1 | 4/2002 | Yurek et al. | |
| 6,391,050 B1 | 5/2002 | Broome | |
| 6,443,971 B1 | 9/2002 | Boylan et al. | |
| 6,447,540 B1 | 9/2002 | Fontaine et al. | |
| 6,485,501 B1 * | 11/2002 | Green | 606/200 |
| 6,517,550 B1 * | 2/2003 | Konya et al. | 606/113 |
| 6,527,746 B1 | 3/2003 | Oslund et al. | |
| 6,537,294 B1 * | 3/2003 | Boyle et al. | 606/200 |
| 6,537,295 B2 | 3/2003 | Petersen | |
| 6,755,846 B1 | 6/2004 | Yadav | |
| 6,893,451 B2 | 5/2005 | Cano et al. | |
| 2002/0004667 A1 | 1/2002 | Adams et al. | |
| 2002/0029075 A1 | 3/2002 | Leonhardt | |
| 2002/0032461 A1 | 3/2002 | Marshall | |
| 2002/0042626 A1 | 4/2002 | Hanson et al. | |
| 2002/0082525 A1* | 6/2002 | Oslund et al. | 600/585 |
| 2003/0093106 A1* | 5/2003 | Brady et al. | 606/194 |
| 2003/0212429 A1* | 11/2003 | Keegan et al. | 606/200 |

FOREIGN PATENT DOCUMENTS

| | | |
|---|---|---|
| EP | 0968688 | 1/2000 |
| FR | 2652267 | 9/1989 |
| WO | WO 98/33443 A1 | 8/1998 |
| WO | WO 99/49808 A1 | 10/1999 |
| WO | WO 99/56801 A2 | 11/1999 |
| WO | WO 00/16705 A1 | 3/2000 |
| WO | WO 01/08743 A1 | 2/2001 |
| WO | WO 01/66178 A1 | 9/2001 |
| WO | WO 01/80777 A2 | 11/2001 |

* cited by examiner

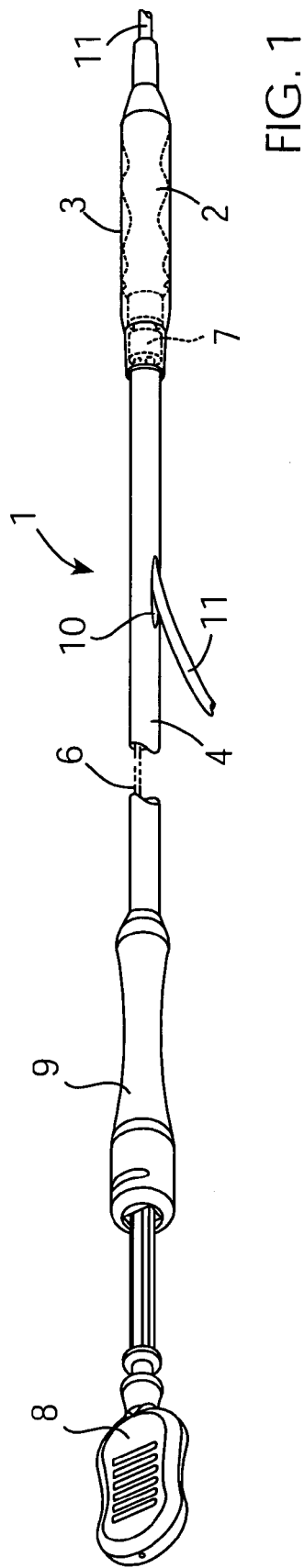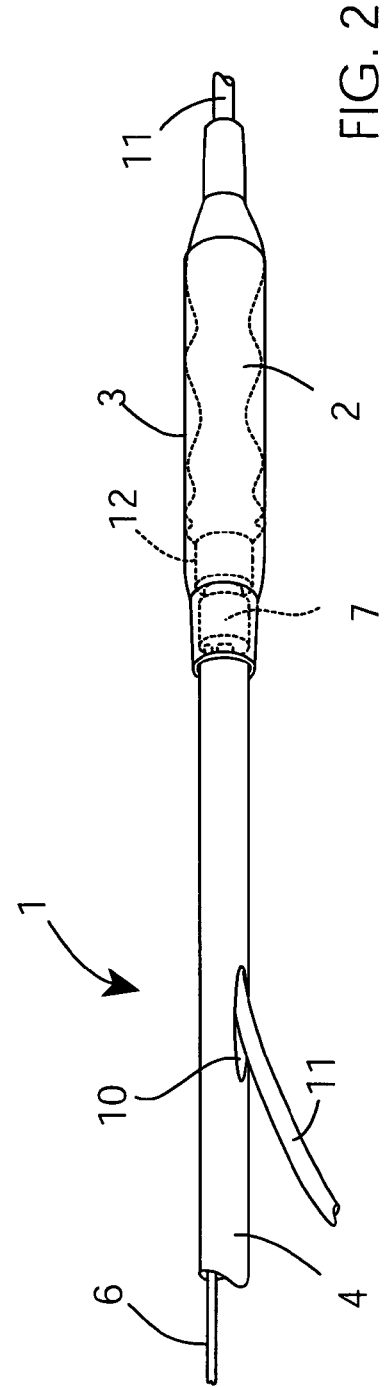

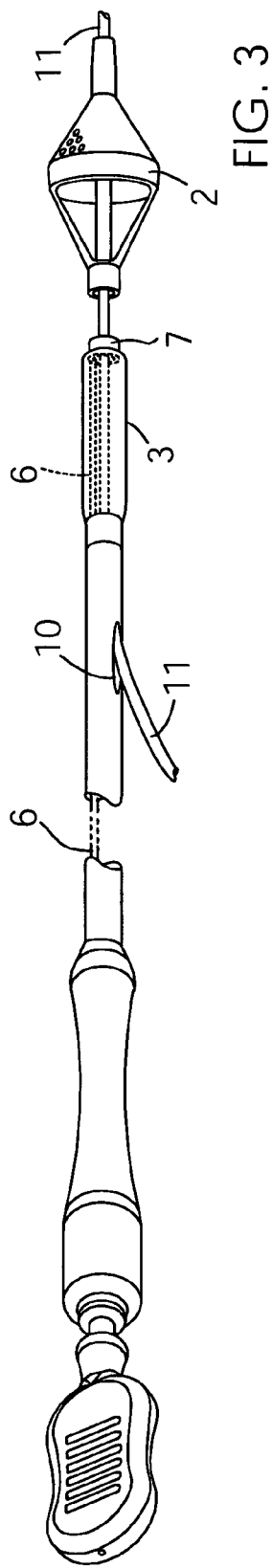
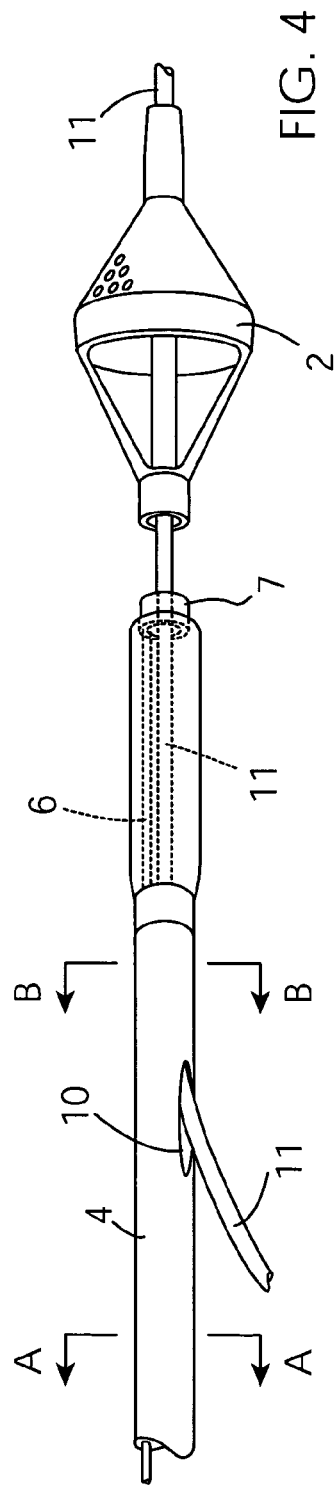
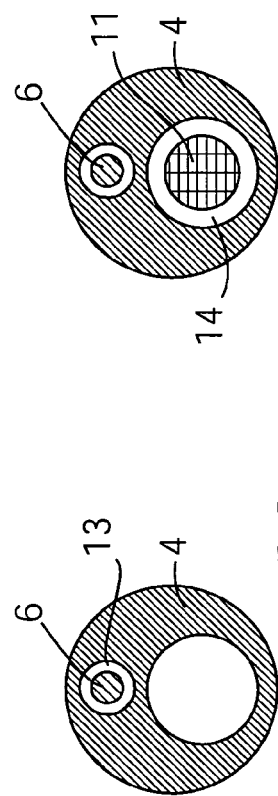
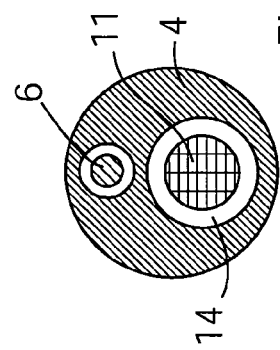
FIG. 3
FIG. 4
FIG. 5
FIG. 6

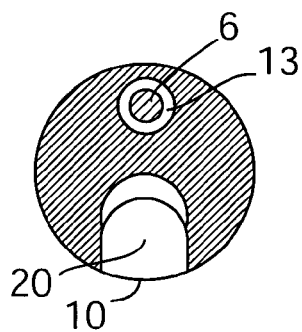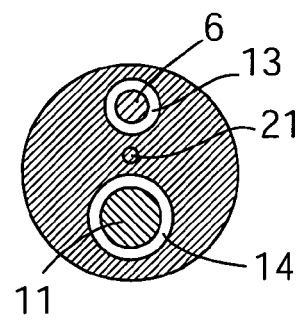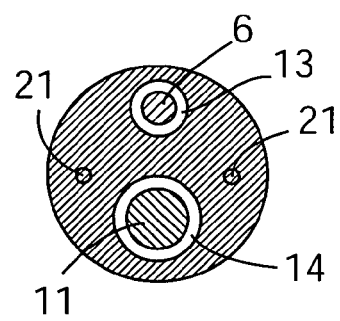
FIG. 7  FIG. 8  FIG. 9
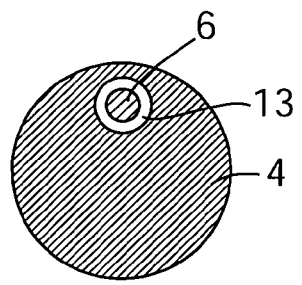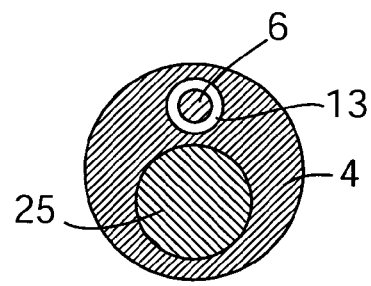
FIG. 10  FIG. 11
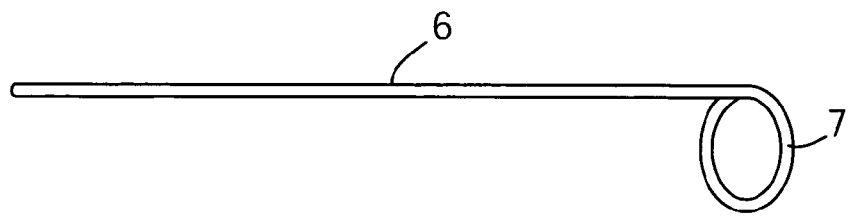
FIG. 23

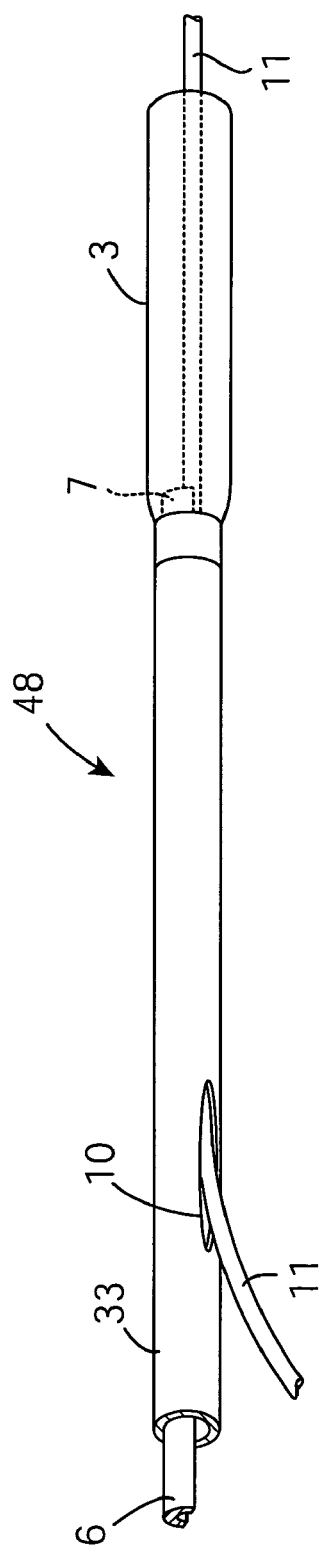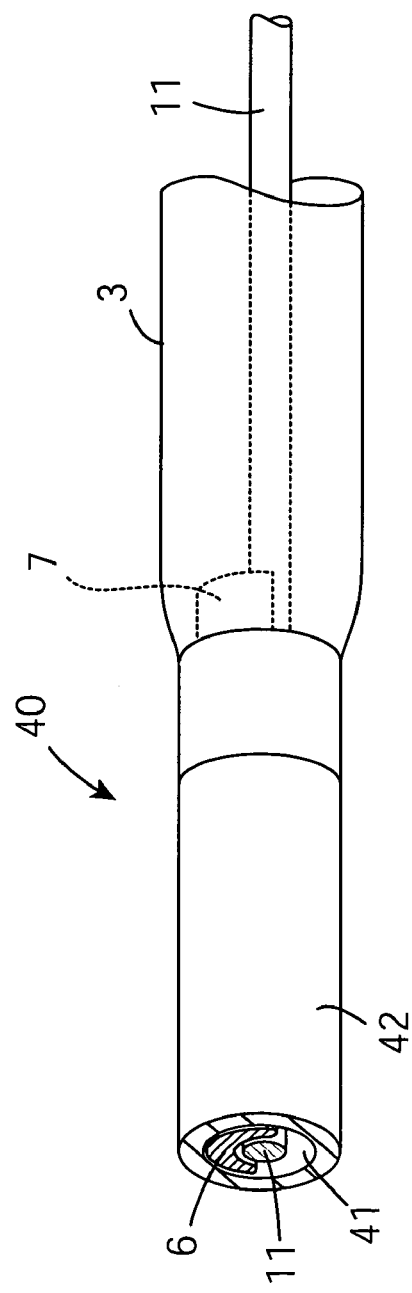

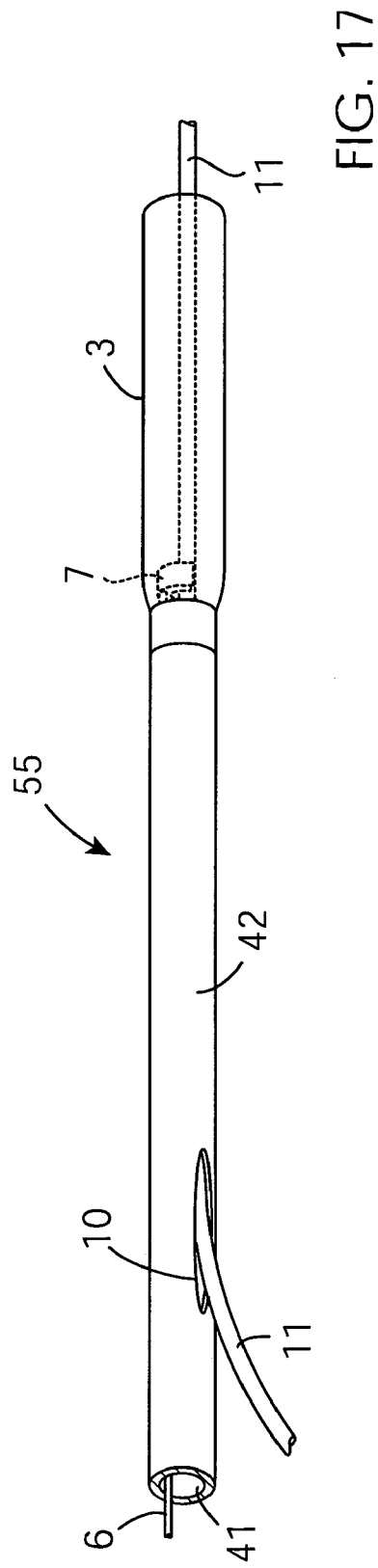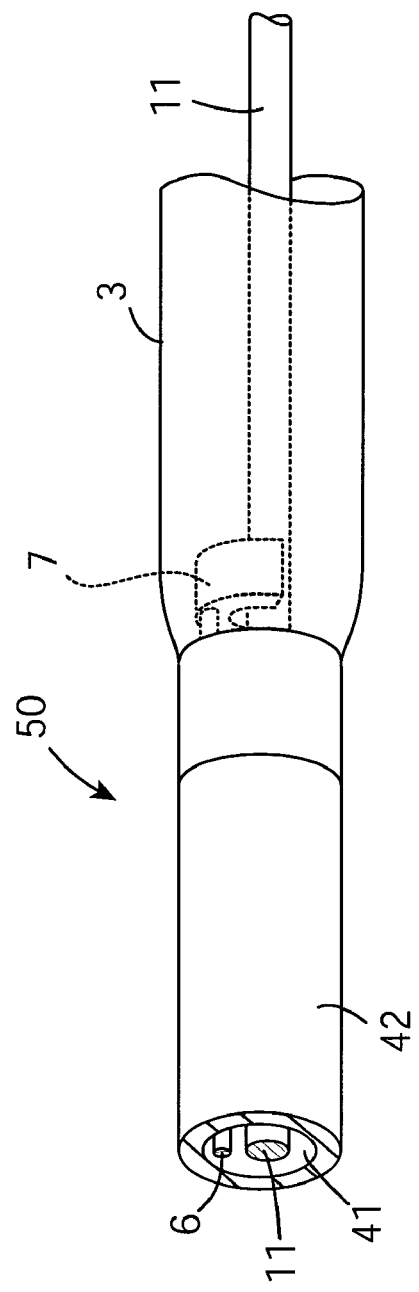

CATHETER

CROSS-REFERENCE TO RELATED APPLICATIONS

This application is related to, and claims the benefit of, the following patent applications, namely: IE Patent Application No. 2001/0591, filed Jun. 27, 2001; and U.S. Patent Application No. 60/301,820, filed Jul. 2, 2001; all of which are hereby incorporated herein by reference in their entirety.

FIELD OF THE INVENTION

This invention relates to a delivery catheter for delivering an embolic protection filter to a desired site in a vasculature, and for deploying the filter at the desired site. In particular this invention relates to a delivery catheter, which is configured to facilitate rapid exchange of the catheter over a guidewire during both delivery and deployment of the filter.

Exchange of a catheter over a guidewire using a rapid exchange arrangement enables an interventional procedure to be performed by a single operator in a fast, efficient manner.

This invention is aimed at providing a catheter which will facilitate both delivery and deployment of an embolic protection filter.

SUMMARY OF THE INVENTION

According to the invention there is provided a delivery catheter comprising:—
- a catheter shaft defining a reception space for a filter; and
- an operating element extending through the catheter shaft for engagement with a filter in the reception space to facilitate deployment of the filter from within the reception space upon movement of the operating element relative to the catheter shaft from a delivery configuration to a deployment configuration;
- along at least a portion of the length of the operating element, the cross-sectional area of the operating element being small relative to the cross-sectional area of the catheter shaft.

In one embodiment of the invention a guidewire opening is provided in the catheter shaft, the guidewire opening being located a substantial distance distally of a proximal end of the catheter shaft for rapid exchange of the catheter over a guidewire. Preferably the cross-sectional area of the operating element is small relative to the cross-sectional area of the catheter shaft in the region of the guidewire opening. Ideally in the delivery configuration the cross-sectional area of the operating element is small relative to the cross-sectional area of the catheter shaft for a distance of at least 10 mm proximally of the guidewire opening. Most preferably in the delivery configuration the cross-sectional area of the operating element is small relative to the cross-sectional area of the catheter shaft for a distance of at least 20 mm proximally of the guidewire opening. Desirably in the delivery configuration the cross-sectional area of the operating element is small relative to the cross sectional area of the catheter shaft for a distance of at least 30 mm proximally of the guidewire opening. In a particularly preferred case in the delivery configuration the cross-sectional area of the operating element is small relative to the cross-sectional area of the catheter shaft for a distance of at least 40 mm proximally of the guidewire opening.

In another embodiment the diameter of the operating element is in the range of from 0.008" to 0.015". Preferably the diameter of the operating element is in the range of from 0.01" to 0.012".

The operating element may comprise a control wire. Preferably the operating element comprises a push wire.

In one case the operating element comprises a proximal actuating element, and a distal engagement element for engaging a filter in the reception space. The engagement element preferably comprises a pusher. The pusher may extend fully around the circumference of the engagement element. The pusher may extend partially around the circumference of the engagement element.

In another embodiment the engagement element is attached to the actuating element. The engagement element may be integral with the actuating element.

The engagement element preferably extends distally of the actuating element. The engagement element may define a guidewire lumen therethrough. Ideally the guidewire opening in the catheter shaft is moveable relative to the guidewire lumen of the engagement element upon deployment of a filter from within the reception space.

In one case the catheter shaft is slidably movable relative to the operating element. Preferably the catheter shaft is movable proximally relative to the operating element to deploy a filter from within the reception space.

The catheter shaft may comprise a proximal shaft portion and a distal pod, the pod defining the reception space. The proximal shaft portion is preferably offset in the radial direction from the pod. Ideally the proximal shaft portion is of a smaller diameter than the pod.

In a preferred case the guidewire opening in the catheter shaft faces in a direction substantially parallel to the longitudinal axis of the catheter. Ideally the guidewire opening faces proximally.

The catheter may comprise means to guide passage of a guidewire through the guidewire opening in the catheter shaft. Preferably the means to guide passage comprises a guiding ramp.

In another embodiment the catheter has a guidewire lumen and a lumen for the operating element. The guidewire lumen and the operating element lumen may be provided in a single tube. The guidewire lumen may be provided in a guidewire tube and the operating element lumen may be provided in an operating element tube.

According to another aspect of the invention there is provided a delivery catheter comprising:—
- a catheter shaft defining a reception space for a filter; and
- a control wire extending through a substantial portion of the length of the catheter shaft for engagement with a filter in the reception space to facilitate deployment of the filter from within the reception space upon movement of the catheter shaft relative to the control wire.

In one embodiment of the invention the catheter shaft defines a wire lumen extending from a proximal end of the catheter to the reception space, and the control wire extends through the full length of the wire lumen. The control wire may be a push wire. Preferably the diameter of the wire is in the range of from 0.008" to 0.015". Ideally the diameter of the wire is in the range of from 0.01" to 0.012".

The designs of this invention provide means of achieving very low profile catheter shafts for the delivery of filter systems. These systems allow for the delivery of filter systems wherein the filter is fastened to a guidewire or where the filter is independent of the guidewire. Some conventional systems employ a push tube to achieve filter deployment. These systems are effective but have a number of disadvantages. It is difficult to achieve the highest level of trackability with a tube-based system. This is because the inner and outer tubes tend to form a composite effect in bending and the overall bending stiffness can be high. The composite effect arises because both shafts bend about the same neutral axis.

The designs of this invention overcome these problems and other problems associated with filter delivery systems. In this invention a push wire is used to transmit the force of deployment from the proximal end to the distal end. The wire is guided in a guide lumen throughout its entire length. This guiding function is important as it ensures that the push wire does not buckle under the forces of deployment. The push wire is connected to an engagement element at its distal end. A variety of engagement element designs are possible. In general, the engagement element must engage the filter at one or more points. Preferably the engagement element engages the filter at least two points. More preferably the engagement element is in contact with a circumferential segment of the filter. Most preferably the engagement comprises a hoop shaped element.

The use of a push wire has a number of advantageous features. Firstly the push wire has a very low cross sectional area and this allows the catheter to be constructed to a very low profile. The small diameter also ensures that its bending stiffness contribution to the catheter is low. Bending stiffness is related to the third power of the diameter. A low bending stiffness is generally associated with good trackability properties. The low profile of the push wire helps to ensure that the profile of the overall catheter is low.

Another advantageous feature of the push wire system is the simplicity of the construction of the catheter which leads to a reduction in the cost of manufacture of the catheter.

A variety of shaft constructions are possible with this invention. In one embodiment the catheter shaft is comprised of two lumens. One lumen is dedicated to the push wire and the other lumen provides a pathway for the guidewire. The two lumens may be provided in one tube or two tubes may be employed. The two-tube construction has a number of advantages. Each tube may have a different set of properties. For example the push wire lumen may be constructed from a low friction material while the other lumen may provide for mechanical properties and may include some reinforcement. In another embodiment the tube has multiple layers to its construction. Co-extrusion processes can be employed in the manufacture multi-layer constructions. In another embodiment reinforcement is incorporated in the wall of the tube.

In another embodiment the push wire and the guidewire are accommodated in the same lumen. This embodiment has the advantage of very low profile. With this embodiment the push wire would preferably be coated with a low friction coating such as Teflon to prevent abrasion with the guidewire. It is also possible with this embodiment to use non-circular wires.

In another embodiment multiple push wires are employed. The advantage of this embodiment is that each wire has its own neutral axis and thus greater flexibility can be achieved.

Reducing the coefficient of friction between the push wire and the wall of the catheter is very important. A variety of designs can be employed to achieve a low friction relative movement. Firstly the push wire can be coated with a low friction coating. PTFE or a lubricious coating is most preferred. Hydrophilic coatings are the most preferred lubricious coatings. Alternatively the push wire may be covered with a lubricating fluid or gel. Likewise the inner surface of the catheter lumen should have a low friction coating or be manufactured from a low friction material. Preferably the tubing is lined with PTFE or a lubricious coating as described above.

Controlling the tolerance between the push wire and its lumen is important in preventing unnecessary frictional forces. Preferably the annular gap is between 0.0004" and 0.005". More preferably the annular gap is between 0.0007" and 0.002".

BRIEF DESCRIPTION OF THE DRAWINGS

The invention will be more clearly understood from the following description thereof given by way of example only, with reference to the accompanying drawings, in which:—

FIG. 1 is a perspective view of a delivery catheter of the invention with a filter located in a distal pod;

FIG. 2 is an enlarged view of a distal section of the catheter of FIG. 1;

FIG. 3 is a perspective view of the catheter of FIG. 1 with a filter deployed;

FIG. 4 is an enlarged view of a distal section of the catheter and the filter of FIG. 3;

FIG. 5 is a cross-sectional view of the line A-A in FIG. 4;

FIG. 6 is a cross-sectional view of the line B-B in FIG. 4;

FIG. 7 is a cross-sectional view at an exit port of a catheter;

FIGS. 8 and 9 are cross-sectional views of alternative constructions of shaft with reinforcing means;

FIGS. 10 and 11 are cross-sectional views of alternative shaft constructions;

FIGS. 12 to 17 are side views of distal sections of alternative delivery catheters of the invention;

FIG. 23 is a perspective view of a push wire of the catheter.

DETAILED DESCRIPTION

Figure 13:
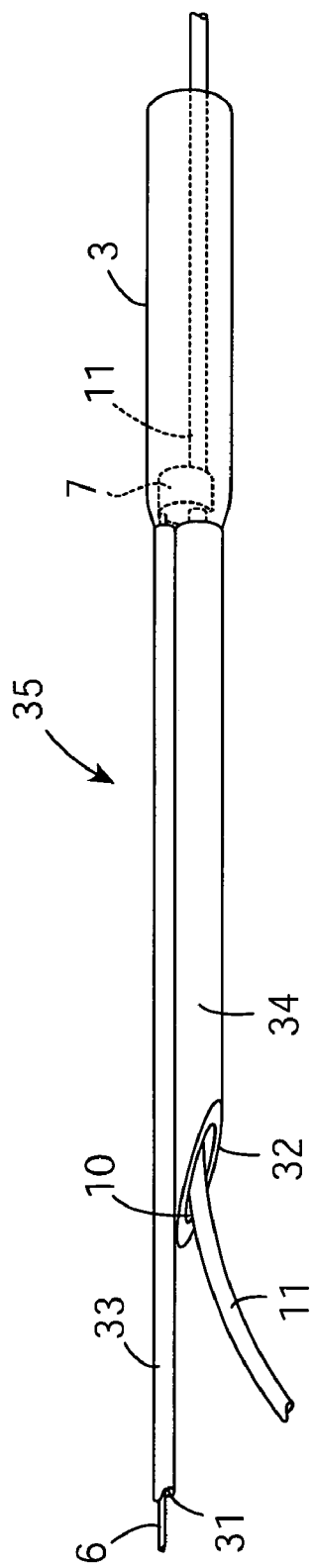

Referring initially to FIGS. 1 to 6 there is illustrated a delivery system 1 of the invention for delivery of a filter 2. The filter 2 is in a collapsed delivery configuration in FIGS. 1 and 2. The filter 2 is shown in its collapsed state in a pod 3 of the delivery catheter 1. The catheter 1 comprises a shaft 4, which has a distal end and a proximal end. The distal end comprises a pod 3 for receiving the collapsed filter 2. The proximal end of the shaft is attached to a handle element 9. A push wire 6 has a proximal end and a distal end. The push wire 6 has an engagement element 7 at its distal end. The push wire 6 is connected to a deployment tab 8 at the proximal end. Retracting the handle element 9 relative to the deployment tab 8 deploys the filter. This movement has the effect of retracting the pod 3 and shaft 4 relative to the push wire 6, the engagement element 7 and the filter 2. The shaft 4 has an exit port 10 located a substantial distance from its proximal end. A guidewire 11 passes through central axis of the filter 2, and exits the guidewire exit port 10. The exit port 10 comprises an opening in the sidewall of the shaft tubing. The guidewire lumen may be blanked proximal to the exit port 10 to ensure that the guidewire 11 does not snag at the exit port.

An enlarged view of the distal end of the catheter 1 in its delivery configuration is shown in FIG. 2. The relationship between the engagement element 7, the pod 3 and the proximal end of the filter 12 will be apparent, particularly from this figure.

The delivery catheter is shown in the deployed configuration in FIG. 3. In this case, the filter 2 is shown on the guidewire 11 in its expanded configuration. It will be noted when FIG. 3 is compared to FIG. 1 that deployment is achieved through a retraction of the handle element 9, the shaft 4 and the pod 3. The push wire 6 and engagement element 7 are visible extending distal to the end of the pod 3. The push wire 6 and engagement element are integral in one embodiment. In this embodiment (see also FIG. 23) the end of the push wire 6 may be formed into a hoop 7 and the hoop provides an engagement surface with the filter. In another embodiment the engagement element has an annular aspect. In another embodiment the engagement serves the dual function as engagement element and marker band. The push wire 6 and engagement element 7 may be attached by a number of processes. Welding, brazing, soldering and bonding are preferred processes.

An enlarged view of the distal end of the catheter in its deployed configuration is shown in FIG. 4.

Sectional views of the catheter 1 at A-A and B-B are shown in FIG. 5 and FIG. 6 respectively. The sectional views show the push wire 6 in a first lumen 13 in both views. The guidewire is shown in guidewire lumen 14 in the distal section B-B only. As the guidewire II exits at the exit port 10 the guidewire lumen 14 is empty in the proximal section. This design provides a catheter which can be easily converted from an over-the-wire product to a rapid exchange device.

FIG. 7 shows one means by which an exit port 10 can be manufactured. The outer wall of the catheter shaft in the region of the exit port 10 is reformed so as to provide an exit ramp 20 without any significant weakening of the shaft. This approach eliminates the need to skive material from the shaft.

Alternative cross sections are shown in FIG. 8 and FIG. 9. In both these embodiment reinforcements 21 are shown in the wall of the shafts. The configuration shown in FIG. 8 is particularly desirable as the reinforcements 21 are shown close to the center of the section. This will minimize the impact of the reinforcement on the bending stiffness of the shaft.

In another embodiment the guidewire lumen 14 ends at the exit port. The proximal section of the shaft 4 may be solid as shown in FIG. 10 or it may contain reinforcement 25 as shown in FIG. 11. The use of reinforcement 25 in the proximal section of the catheter is particularly desirable as it provides excellent push to the user. The proximal section generally does not need to be as flexible as the distal end. The solid proximal embodiment provides additional cross sectional area in the proximal region for push transmission. In the arrangement of FIG. 10 a solid proximal shaft may be joined to a dual lumen distal shaft.

Figure 12:
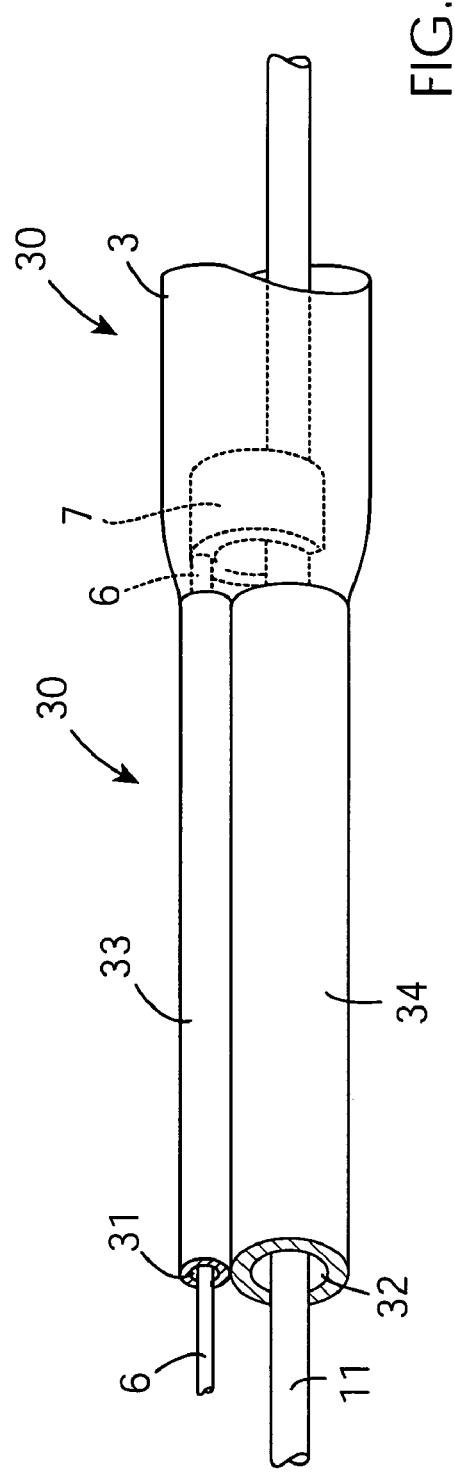

FIG. 12 and FIG. 13 show further catheters 30, 35 of the invention. In this embodiment a push wire lumen 31 and a guidewire lumen 32 are provided in two separate tubes 33, 34. In one embodiment the tubes 33, 34 are joined at their point of contact. In another embodiment the tubes are joined at intervals along the length of the tubes 33, 34. The pod 3 is shown attached to both tubes 33, 34 at the distal end. The catheter 35 of FIG. 13 particularly highlights a rapid exchange adoption of this two-tube system 33, 34. The exit port 10 of this configuration is desirable as the guidewire 11 exits the exit port 10 parallel to the catheter shaft.

FIG. 14 shows another catheter 40 according to the invention. In this configuration the push wire 6 and the guidewire 11 share the same lumen 41 in a shaft 42. The push wire 6 in this case has a non-circular cross section. In this case, the push wire 6 cross section is kidney shaped. This shape provides efficient use of the available lumen space. FIG. 15 shows a catheter 48 similar to that of FIG. 14 in a rapid exchange format. FIG. 16 shows a catheter 50, the guidewire 11 and the push wire 6 in the same lumen also. In this embodiment the push wire 6 is of circular cross section. FIG. 17 shows a catheter 55 with the features of the catheter of FIG. 16 in a rapid exchange construction.

Figure 18:
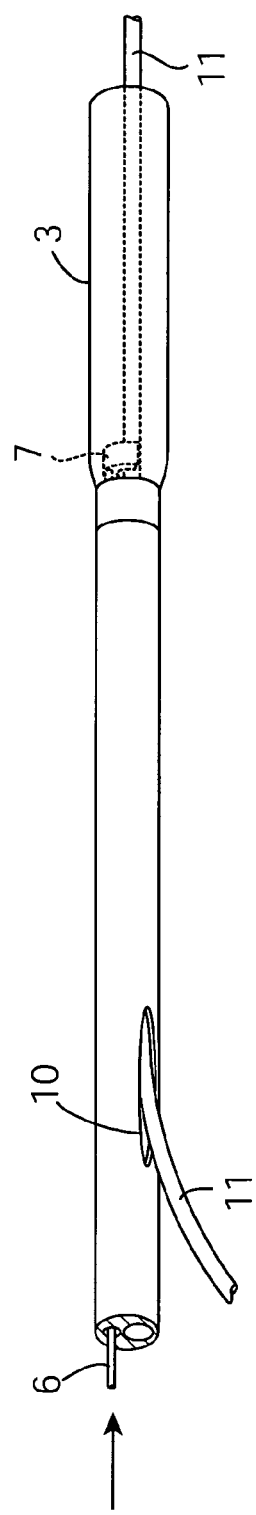
FIG. 18 is a side view of another delivery catheter with a push wire in a delivery configuration.
Figure 19:
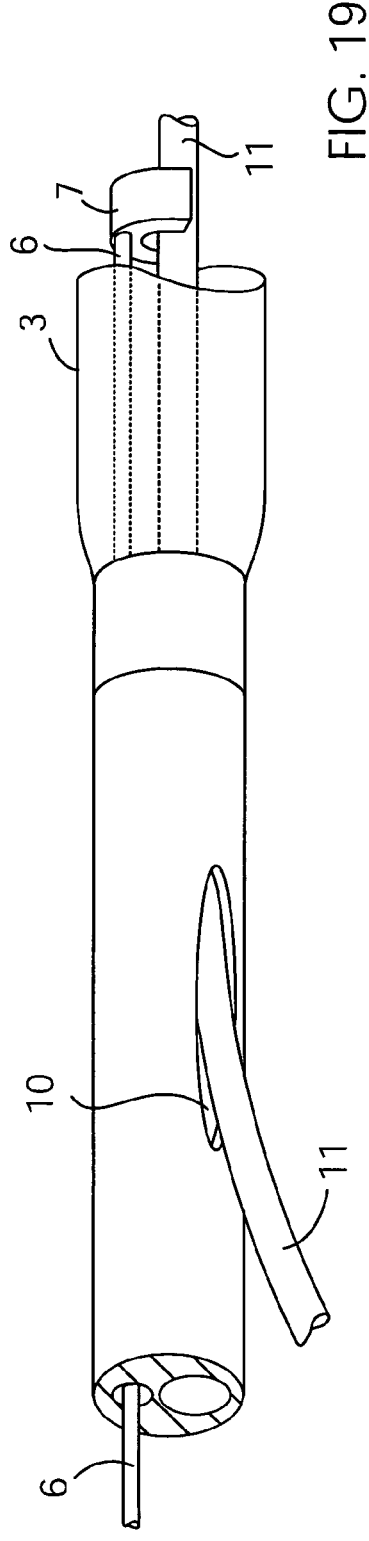
FIG. 19 is a side view of the catheter of FIG. 18 with the push wire in a deployed configuration.

The operation of the deployment system of the invention is shown in the absence of a filter in FIG. 18 and FIG. 19. FIG. 18 is an exploded view with the push wire 6 in its delivery position. FIG. 19 is an exploded view of the push wire 6 and engagement element 7 in the deployed configuration.

Figure 20:
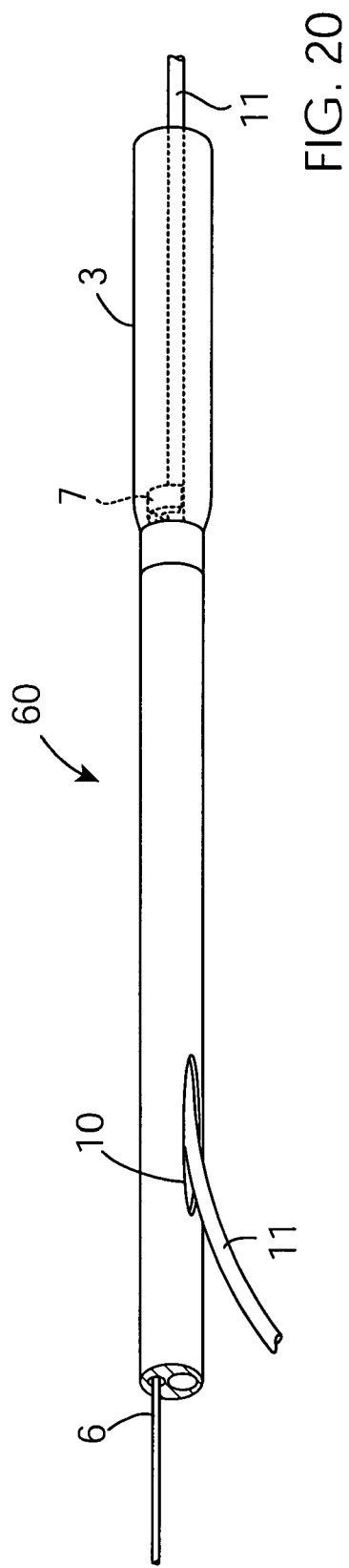
FIG. 20 is a side view of a further delivery catheter with a push wire in a delivery configuration.
Figure 21:
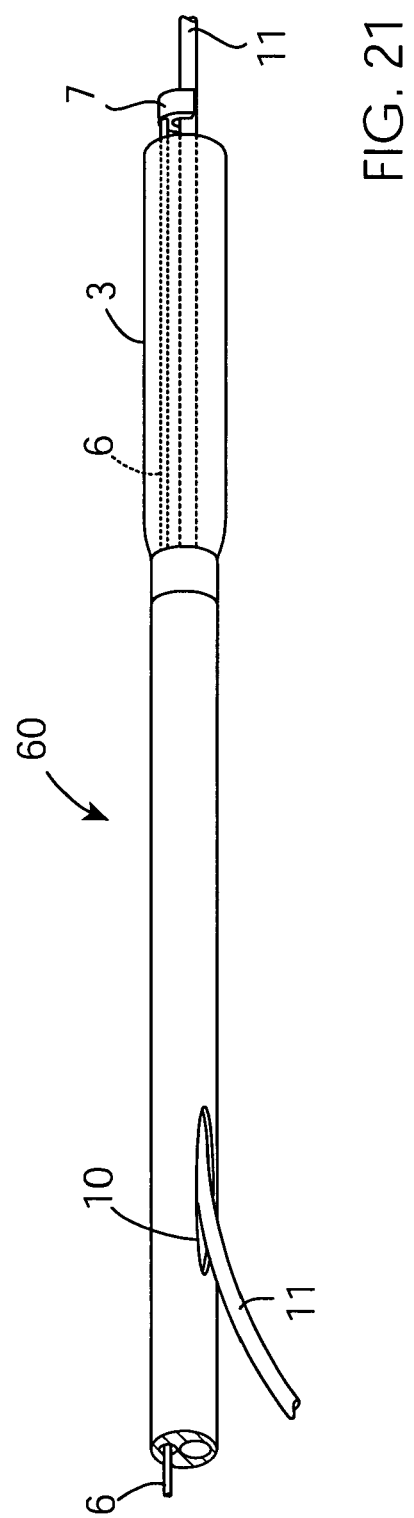
FIG. 21 is a side view of the catheter of FIG. 20 with the push wire in a deployed configuration.

FIG. 20 is an exploded view of a catheter 60 in its delivery position. FIG. 21 is an exploded view of the catheter 60 in the deployed configuration.

Figure 22:
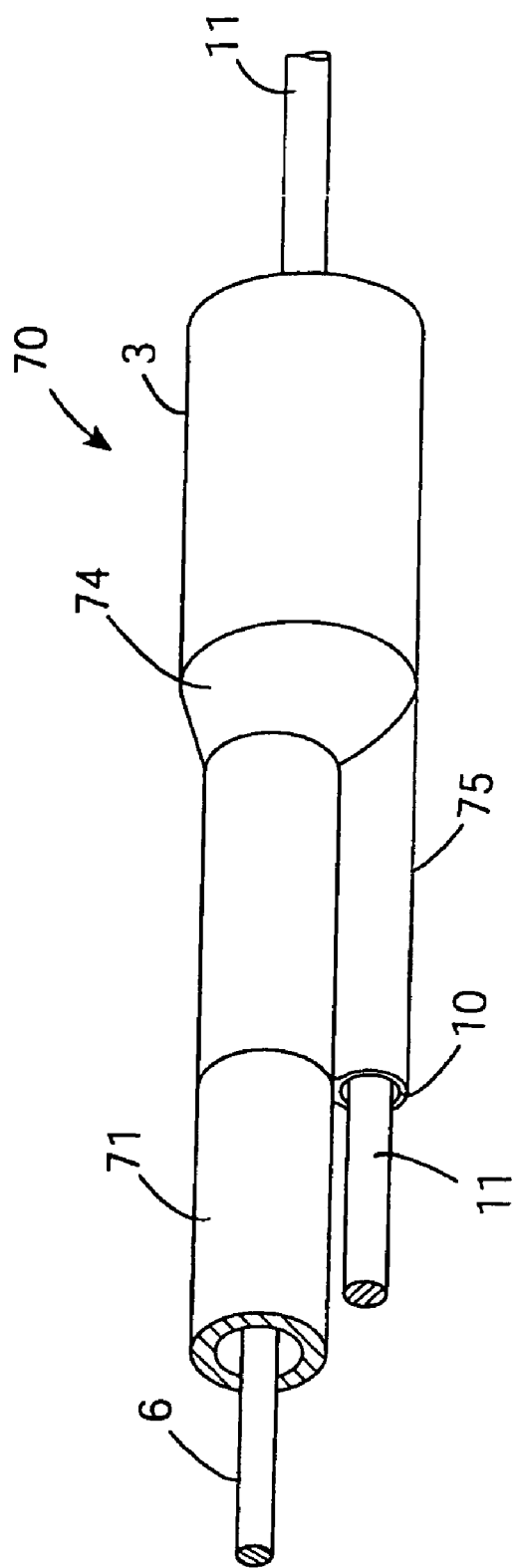
FIG. 22 is a side view of a distal section of another delivery catheter.

Another catheter 70 is shown in FIG. 22. In this arrangement the catheter 70 has a catheter shaft 71 comprising a single lumen tube. The tube lumen is used to protect the push wire 6. The guidewire 11 exits the catheter at the proximal end of the pod 3. The pod 3 is bonded to shaft 71 around a portion of its length. The remaining portion of the pod circumference is employed in defining a guidewire lumen 75. The offset aspect of the engagement element as described in previous embodiments is used in this embodiment to direct the guidewire 11 to the exit port 10. The advantage of this construction is that the proximal shaft 71 can be highly trackable and of exceptionally low profile. Push wires 6 whose diameter is of the order of 0.008" to 0.012" can be effectively employed with this invention. Thus, exceptional shaft profile can be achieved. Another advantage of this arrangement is that the guidewire 11 exists the exit port 10 in a parallel fashion.

The delivery catheter according to the invention is suitable for delivery of an embolic protection filter through a vasculature over a guidewire and deployment of the filter at a desired site in the vasculature.

The delivery catheter is suitable for rapid exchange over a guidewire during delivery and deployment of an embolic protection filter in a vasculature, and during withdrawal of the delivery catheter after deployment. In particular, the delivery catheter comprises a catheter body which extends between a proximal end and a distal end, and the catheter body defines an opening in a sidewall of the catheter body, and an opening at the distal end of the catheter body. A guidewire lumen extends between these openings to enable passage of a guidewire through the lumen, and thereby facilitate rapid exchange of the delivery catheter over the guidewire.

A distal portion of the catheter body defines a reception space for an embolic protection filter during delivery of the filter through a vasculature, and at least one elongate actuator is provided extending along the catheter body to facilitate deployment of the filter from within the reception space.

The delivery catheter is particularly suitable for delivery and deployment of a filter, which is received within the reception space but is separate and independent of the delivery catheter, and which is separate and independent of the rapid exchange guidewire. One example of this type of filter is the embolic protection filter described in International patent application number PCT/IE01/00053, the relevant content of which are incorporated herein by reference.

In the region adjacent the guidewire opening in the sidewall of the catheter body, the actuator has a small cross-sectional area relative to the overall cross-sectional area of the delivery catheter. By providing such a thin, elongate actuator, this ensures that the guidewire opening in the sidewall of the catheter body, which serves as the rapid exchange port for a guidewire, will not be obstructed or occluded by manipulation of the actuator upon deployment of a filter from within the reception space.

The delivery catheter according to the invention is particularly suitable for delivery and deployment of an expandable embolic protection filter. In this case, the distal portion of the catheter body is provided by a sheath which restrains the embolic protection filter in a low-profile, collapsed configuration within the reception space during delivery to a desired site in a vasculature. The sheath is preferably thin-walled to minimise the overall crossing profile of the delivery catheter, especially during delivery of the embolic protection filter.

The method of collapsing the filter and loading the filter into the reception space is similar to that described in International patent application number PCT/IE01/00052, the relevant contents of which are incorporated herein by reference.

A guidewire is inserted into a vasculature and advanced through the vasculature until the guidewire has crossed a site of interest in the vasculature. A typical site of interest is a stenosed or diseased region of the vasculature. The delivery catheter is then threaded over the guidewire by inserting the proximal end of the guidewire into the guidewire lumen at the distal end and out of the lumen through the proximal guidewire opening. The catheter is advanced over the guidewire in a rapid exchange manner until the reception space is located downstream of the stenosis.

When the filter has been fully deployed at the desired site in the vasculature, the delivery catheter is withdrawn from the vasculature over the guidewire in a rapid exchange manner to leave the deployed filter in place in the vasculature.

The movement of the push wire 6 does not occlude the proximal guidewire opening, or in any way interfere with passage of the guidewire through the guidewire lumen. Thus, rapid exchange of the delivery catheter over the guidewire is possible during deployment of the filter also.

In this manner, the filter may be accurately deployed in a controlled manner without the overall crossing profile of the delivery catheter being adversely effected. In particular, no bulging or accordioning of the catheter occurs during the deployment action.

The delivery catheter according to the invention is particularly suitable for delivering an embolic protection filter in a downstream direction to a desired location in a vasculature, and deploying the filter at the desired location.

The invention is not limited to the embodiments hereinbefore described which may be varied in detail.

The invention claimed is:

1. A delivery catheter system comprising:
a guidewire;
an embolic protection filter disposed over the guidewire, the filter comprising a proximal end, a distal end, an expanded profile in a deployed configuration and a low-profile in a collapsed configuration for delivery; and
a delivery catheter for delivering the filter over the guidewire in the collapsed configuration to a treatment site and deploying the filter at the treatment site into the deployed configuration;
the delivery catheter comprising:
a catheter body having a proximal end and a distal end, the catheter body comprising a guidewire lumen and an operating lumen, the guidewire lumen extending parallel to the operating lumen, the guidewire disposed within the guidewire lumen;
a pod extending distally from the distal end of the catheter body, the pod being fixed to the catheter body and having an outer diameter greater than an outer diameter of the catheter body, the pod having a lumen defining a tubular reception space for receiving and maintaining the filter in the collapsed configuration;
the longitudinal axis of the catheter shaft is offset in the radial direction from the longitudinal axis of the control wire;
an operating wire slidably disposed within the operating lumen and extending into the pod, the operating wire having a proximal end and a distal end; and
an engagement element extending from and fixed to the distal end of the operating wire, the engagement element comprising a proximal end and a distal end, the engagement element slidably disposed within the lumen of the pod, the engagement element having an outer diameter that is greater than an outer diameter of the operating wire but less than an inner diameter of the lumen of the pod, the distal end of the engagement element slidably abuts the proximal end of the filter to deploy the filter from within the tubular reception space.

2. A catheter system as claimed in claim 1 wherein a guidewire opening is provided in the catheter body, the guidewire opening being located a substantial distance distally of a proximal end of the catheter body for rapid exchange of the delivery catheter over the guidewire, the guidewire opening in communication with the guidewire lumen.

3. A delivery catheter system as claimed in claim 2 wherein the cross-sectional area of the operating wire is small relative to the cross-sectional area of the catheter body in the region of the guidewire opening.

4. A delivery catheter system as claimed in claim 3 wherein in the delivery configuration the cross-sectional area of the operating wire is small relative to the cross-sectional area of the catheter body for a distance of at least 10 mm proximally of the guidewire opening.

5. A delivery catheter system as claimed in claim 4 wherein in the delivery configuration the cross-sectional area of the operating wire is small relative to the cross-sectional area of the catheter body for a distance of at least 20 mm proximally of the guidewire opening.

6. A delivery catheter system as claimed in claim 5 wherein in the delivery configuration the cross-sectional area of the operating wire is small relative to the cross-sectional area of the catheter body for a distance of at least 30 mm proximally of the guidewire opening.

7. A delivery catheter system as claimed in claim 6 wherein in the delivery configuration the cross-sectional area of the operating wire is small relative to the cross-sectional area of the catheter body for a distance of at least 40 mm proximally of the guidewire opening.

8. A delivery catheter system as claimed in claim 2 wherein the guidewire opening in the catheter body faces in a direction substantially parallel to the longitudinal axis of the delivery catheter.

9. A delivery catheter system as claimed in claim 8 wherein the guidewire opening faces proximally.

10. A delivery catheter system as claimed in claim 2 wherein the delivery catheter comprises means to guide passage of the guidewire through the guidewire opening in the catheter body.

11. A delivery catheter system as claimed in claim 10 wherein the means to guide passage comprises a guiding ramp.

12. A delivery catheter system as claimed in claim 1 wherein the cross-sectional area of the operating wire is in the range of from 0.008" to 0.015".

13. A delivery catheter system as claimed in claim 12 wherein the cross-sectional area of the operating wire is in the range of from 0.01" to 0.012".

14. A delivery catheter system as claimed in claim 1 wherein the operating wire comprises a control wire.

15. A delivery catheter system as claimed in claim 14 wherein the operating wire comprises a push wire.

16. A delivery catheter system as claimed in claim 15, wherein a cross section of the push wire is kidney shaped.

17. A delivery catheter system as claimed in claim 1 wherein the operating wire comprises a proximal actuating element, and the engagement element is slidable distally for engaging the filter in the reception space.

18. A delivery catheter system as claimed in claim 17 wherein the engagement element is a pusher.

19. A delivery catheter system as claimed in claim 18 wherein the pusher extends fully around the circumference of the engagement element.

20. A delivery catheter system as claimed in claim 18 wherein the pusher extends partially around the circumference of the engagement element.

21. A deliver catheter system as claimed in claim 1 wherein the engagement element is integral with the operating wire.

22. A delivery catheter system as claimed in claim 1 wherein the engagement element defines a guidewire lumen therethrough for passage of the guidewire.

23. A delivery catheter system as claimed in claim 22 wherein a guidewire opening in the catheter body is moveable relative to the guidewire lumen of the engagement element upon deployment of the filter from within the reception space.

24. A delivery catheter system as claimed in claim 1 wherein the catheter body is slidably movable relative to the operating wire.

25. A delivery catheter system as claimed in claim 1 wherein the catheter body is movable proximally relative to the operating wire to deploy the filter from within the reception space.

26. A deliver catheter as claimed in claim 1 wherein the catheter body is of a smaller diameter than the pod.

27. A delivery catheter system as claimed in claim 1 wherein the guidewire lumen and the operating element lumen are provided in a single tube.

28. A delivery catheter system as claimed in claim 1 wherein the guidewire lumen is provided in a guidewire tube and the operating element lumen is provided in an operating element tube.

29. A delivery catheter system as claimed in claim 1, wherein a radius of the operating lumen is smaller than a radius of the guidewire lumen to ensure that the operating wire does not buckle under pressure when facilitating deployment of the filter.

30. A delivery catheter system as claimed in claim 1, wherein a radius of the guidewire is larger than a radius of the operating wire.

31. A delivery catheter system as claimed in claim 1, wherein a cross-sectional surface area of the engagement element is larger than a cross-sectional surface area of the operating wire.

32. A method of using the delivery catheter system of claim 1, comprising:
 inserting the guidewire into a vasculature and advancing the guidewire passed a site of interest in the vasculature;
 threading the delivery catheter over the guidewire by inserting a proximal end of the guidewire into the guidewire lumen;
 advancing the delivery catheter over the guidewire until the reception space is located downstream of the site of interest, and
 deploying the filter by relative movement of the operating wire and catheter body.

* * * * *